United States Patent [19]

Sagawa et al.

[11] 3,975,417
[45] Aug. 17, 1976

[54] PROCESS FOR PRODUCING HALOGENATED ORGANOTIN COMPOUNDS

[75] Inventors: Seiji Sagawa, Hirakata; Osamu Kimura, Toyonaka; Kenji Sekimori, Machida; Fumiyuki Ito, Hatogaya, all of Japan

[73] Assignees: Sumitomo Chemical Company, Osaka; Kyodo Chemical Company, Ltd., Tokyo, both of Japan

[22] Filed: Oct. 21, 1974

[21] Appl. No.: 516,868

Related U.S. Application Data

[63] Continuation-in-part of Ser. No. 354,138, April 24, 1973, abandoned.

[30] Foreign Application Priority Data

Apr. 28, 1972 Japan.............................. 47-43129
Aug. 3, 1972 Japan.............................. 47-78109

[52] U.S. Cl. ............................................ 260/429.7
[51] Int. Cl.² ............................................ C07F 7/22
[58] Field of Search .............................. 260/429.7

[56] References Cited
UNITED STATES PATENTS

| | | |
|---|---|---|
| 3,340,283 | 9/1967 | Glaskey .......................... 260/429.7 |
| 3,387,012 | 6/1968 | Jasching ......................... 260/429.7 |
| 3,404,167 | 10/1968 | Gray et al. ...................... 260/429.7 |
| 3,414,595 | 12/1968 | Oakes ............................. 260/429.7 |
| 3,440,255 | 4/1969 | Matsuda et al. ................. 260/429.7 |
| 3,519,665 | 7/1970 | Molt et al. ....................... 260/429.7 |
| 3,519,667 | 7/1970 | Molt et al. ....................... 260/429.7 |
| 3,745,183 | 7/1973 | Katsumura et al. ............. 260/429.7 |

*Primary Examiner*—Helen M. S. Sneed
*Attorney, Agent, or Firm*—Wenderoth, Lind & Ponack

[57] ABSTRACT

A process for the production of an octyltin chloride of the formula,

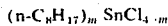

$$(n\text{-}C_8H_{17})_m SnCl_{4-m}$$

wherein $m$ is an integer of 1 to 3, which comprises reacting n-octyl chloride with metallic tin in an organic solvent in the presence of (1) either a mixture of a phosphorus compound with an amine, or a phosphorus compound having a nitrogen atom in the molecule, and (2) at least one of bromine, a bromine compound, iodine and an iodine compound. The octyltin chlorides are useful for the production of stabilizers for polyvinyl chloride.

6 Claims, No Drawings

PROCESS FOR PRODUCING HALOGENATED ORGANOTIN COMPOUNDS

This application is a continuation-in-part of copending application, Ser. No. 354,138, filed on Apr. 24, 1973, now abandoned.

The present invention relates to a method for preparing halogenated organotin compounds, namely n-octyltin chlorides.

The halogenated organotin compounds are important intermediates. For example, they are hydrolyzed by a known method to give corresponding organotin oxides, which are useful for the production of various stabilizers for halogen-containing synthetic resins such as polyvinyl chloride.

A number of methods for preparing halogenated alkyltin compounds, e.g. the Grignard Method, the Wultz Method and the like, are known, amd among them the most convenient and economically advantageous methods are those in which halogenated compounds are reacted directly with metallic tin.

Methods for obtaining halogenated alkyltin compounds by using alkyl iodides as an alkylating agent have already been accomplished as an industrial process.

However, as this method needs the use of expensive alkyl iodides, the recovery of iodine is economically indispensable, and moreover, the yields of alkyltin iodides having a long-chain alkyl group having above 8 carbon atoms are only at best approximately 80%.

For the above reason, a development of the process has so far been desired in which objective products can be obtained in a high yield by using low-priced chlorides as an alkylating agent.

Many compounds, however, which have been considered to be an effective catalyst in a direct reaction of alkyl iodides with metallic tin are substantially of no effect in reactions of corresponding bromides or chlorides with metallic tin, and therefore the reactions proceed with extreme difficulty, and the rate of conversion of metallic tin into organotin compounds, particularly when chlorides are employed, is quite low except for a very few activated chlorides, e.g. benzylchloride.

The inventors, as a result of extensive studies on avoiding these defects, have surprisingly found that the objective products can be obtained, even if chlorides or bromides are employed as the alkylating agent, in a short time and at a high yield as could never be imagined from conventional knowledge, by adding to the reaction system a nitrogen-containing phosphorus compound or a mixture of a phosphorus compound and an amine compound, and in addition a small amount of at least one member selected from the group consisting of bromine, iodine and compounds thereof.

The present invention thus provides a process for producing an octyltin chloride of the formula,

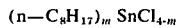

$(n-C_8H_{17})_m SnCl_{4-m}$ wherein $m$ is an integer of 1 to 3, which comprises reacting n-octyl chloride with metallic tin in an organic solvent in the presence of (1) a mixture of a phosphorus compound with an amine compound, or a phosphorus compound having a nitrogen atom in the molecule, and (2) at least one member of bromine, a bromine compound, iodine and an iodine compound.

In carrying out the process of the present invention, as concrete examples of phosphorus compounds of the present invention, the following compounds are included: triphenyl phosphate, triphenyl phosphite, diphenyl phosphorochloridate, triethyl phosphite, tributyl phosphite and tetraethylphosphonium iodide. Of these, the most favorable is triphenyl phosphite.

As the amine compounds used together with the above said phosphorus compounds, the following compounds are included: N-methyl pyrrolidone, quinoline, morpholine, pyridine, dibutylamine, tributylamine, triphenylamine and N,N-dimethylformamide. Of these, the most favorable is N-methyl pyrrolidone.

As the nitrogen-containing phosphorus compounds of the present invention, there are included hexamethylphosphoramide, dimethylphosphoramidic dichloride and tetramethylphosphoramidic chloride. Of these, the most favorable is hexamethylphosphoramide.

Furthermore, as bromine and iodine compounds of the present invention, the following compounds are included: inorganic bromine and iodine compounds which are capable of evolving bromine or iodine at the reaction temperature employed, for example, $PBr_3$, $AlBr_3$, $CuI_2$, $MgI_2$, $MgBr_2$, $ZnBr_2$ and $ZnI_2$.

The organic solvents used in the present process, which also function as an alkylating catalyst, include the following alcohols: n-butyl alcohol, methoxybutyl alcohol, 2-ethylhexyl alcohol, n-octyl alcohol, decyl alcohol and lauryl alcohol. Of these, the favorable ones n-butyl alcohol, 2-ethylhexyl alcohol and n-octyl alcohol.

The amount of n-octyl chloride employed according to the present invention is 1.5 to 5 times by molar ratio based on metallic tin, preferably 2 to 3 times. The reaction is carried out at 130° to 230°C. for 3 to 20 hours under atmospheric or increased pressure, whereby the reaction is completed and the rate of conversion of tin amounts to approximately 100%. The mixture of the amine compound and the phosphorus compound, or the nitrogen-containing phosphorus compound is each used in an amount of at least 0.1% by weight based on the metallic tin, e.g. 0.001 g. to 1.5 g., preferably 0.05 to 1 g., per 1 g. of tin, and bromine, iodine or compounds thereof is each used in an amount of at least 0.01% by weight based on the metallic tin, e.g. 0.0001 g. to g., preferably 0.001 to 0.2 g., per 1 g. of tin.

The solvent is used usually in an amount of 0.1 to 2.0 g., preferably 0.17 to 1.7 g., per 1 g. of tin.

According to the process of the present invention, it is possible to optionally obtain any one of mono-, di- or tri-octyltin compounds in a relatively large amount by changing the amount of phosphorus compounds, amine compounds, nitrogen-containing phosphorus compounds and the organic solvents. For example, more favorable mono- or di-octyltin chloride can selectively be obtained by controlling the amount of organic solvents.

The organic solvents of the present invention also function as an alkylating catalyst as shown in examples hereinafter, and therefore the use thereof is essential. And the reaction system where organic solvents alone and no phosphorus compounds are used has a disadvantage that a tin reaction does not substantially proceed. Bromine, iodine or compounds thereof act particularly effectively as an initiator of the tin reaction.

The phosphorus compounds and the amine compounds of the present invention do not show so highly a catalytic effect when used separately, but show an extremely high synergistic effect when used in combination, and bromine, iodine and compounds thereof are especially effective as an initiator of the tin reaction. Therefore the lack of any one of the above-mentioned conditions can not permit the reaction to proceed completely.

The present invention will now be illustrated in detail with reference to examples which are illustrative but not limitative thereto.

EXAMPLE 1

30 g. of tin foil, 94.2 g. of n-octylchloride, 25 g. of hexamethylphosphoramide, 25 g. of n-octanol and 2 g. of iodine are placed in a 500 ml. flask with four necks equipped with a stirrer, a reflux condenser and a thermometer, heated under reflux at 170° to 185°C. for 4 hours, then 100% of the tin foil is reacted to give a yellow clear reaction mixture. The mixture is distilled under a reduced pressure to recover n-octylchloride, n-octanol and hexamethylphosphoramide which are present in excess, and heated while stirring at 90°C. to 100°C. for 30 minutes with the addition of 100 ml. of conc. hydrochloric acid. The resulting layer of hydrochloric acid is separated to remove inorganic tin compounds therefrom. The mixture of octyltinchlorides thus obtained is separated by a known chemical separation process to give 45.5% of octyltintrichloride, 38.1% of dioctyltindichloride and 11.2% of trioctyltinchloride, the total yield of those three compounds really amounting 94.8% based on the metallic tin employed.

When the above reaction is carried out without adding thereto hexamethylphosphoramide or iodine, the metallic tin does not show any change even when heated at 180°C. for 20 hours. When n-octylalcohol is not added, the rate of conversion of tin alone reaches 100%, however 0%, 21.3% and 27.7% of metallic tin employed are only consumed to produce monooctyltintrichloride, dioctyltindichloride and trioctyltinchloride respectively, the total yield amounting to only 49.0%.

EXAMPLE 2

30 g. of tin foil, 94.2 g. of n-octylchloride, 8.5 g. of hexamethylphosphoramide, 50 g. of n-octanol and 2 g. of iodine are placed in the same apparatus as used in Example 1, heated under reflux at 180° to 185°C. for 10 hours, then 100% of the tin foil is reacted. After the same procedure as given in Example 1, monooctyltintrichloride, dioctyltindichloride and trioctyltinchloride are obtained in the yields of 69.5%, 20.0% and 6.3% respectively, the total yield being 95.8%.

EXAMPLE 3

30 g. of tin foil, 94.2 g. of n-octylchloride, 2.5 g. of hexamethylphosphoramide, 5 g. of n-octanol and 2 g. of iodine are placed in the same apparatus as used in Example 1, heated under reflux at 180° to 190°C. for 4 hours, then 100% of the tin foil is reacted. After the same procedure as given in Example 1, monooctyltintrichloride, dioctyltindichloride and trioctyltinchloride are obtained in the yields of 10.0%, 35.5% and 51.2% respectively, the total yield being 96.7%.

EXAMPLES 4–21

The products and yields thereof which are obtained by reacting, at 180°C. to 190°C., 30 g. of tin foil with 94.2 g. of n-octyl chloride in the presence of materials in the proportion given in Table I are summarized in the Table.

Compounds of the general formula $R_mSnX_{4-m}$ in which $m$ is equal to 4 cannot be obtained in any one of Examples.

Table I

| Ex. No. | Ratio of amount of compounds used | | | | | | Reaction time (hr.) | Rate of conversion of tin (%) | Yields of $R_mSnX_{4-m}$ (%) | | |
|---|---|---|---|---|---|---|---|---|---|---|---|
| | Nitrogen-containing phosphorus compounds | (g.) | Organic solvents | (g.) | $Br_2$, $I_2$ or compounds thereof | (g.) | | | m=1 | m=2 | m=3 |
| 4 | Hexamethylphosphoramide | 25 | n-octyl alcohol | 25 | $I_2$ | 2 | 4 | 100 | 45.5 | 38.1 | 11.2 |
| 5 | Dimethylphosphoramidic dichloride | 25 | " | 25 | " | 2 | 4 | 100 | 43.8 | 37.9 | 12.4 |
| 6 | Hexamethylphosphoramide | 8.5 | " | 50 | " | 2 | 10 | 100 | 69.5 | 20.0 | 6.3 |
| 7 | " | 2.5 | " | 5 | " | 2 | 4 | 100 | 10.0 | 35.5 | 51.2 |
| 8 | Tetramethylphosphoramide chloride | 25 | " | 10 | " | 1 | 5 | 100 | 18 | 55 | 18 |
| 9 | Hexamethylphosphoramide | 25 | 2-ethylhexyl alcohol | 10 | " | 1 | 4 | 100 | 21 | 51 | 20 |
| 10 | " | 25 | methoxybutyl alcohol | 20 | " | 1 | 9 | 100 | 18 | 62 | 10 |
| 11 | " | 25 | lauryl alcohol | 20 | " | 1 | 5 | 100 | 18 | 67 | 6 |
| 12 | Hexamethylphosphoramide | 25 | n-octyl alcohol | 5 | $PBr_3$ | 4 | 12 | 100 | 4 | 73 | 17 |
| 13 | " | 25 | " | 5 | $Br_2$ | 5 | 15 | 100 | 3 | 71 | 16 |
| 14 | " | 15 | " | 5 | $CuI_2$ | 4 | 14 | 100 | 5 | 70 | 15 |
| 15 | " | 25 | 2-ethylhexyl alcohol | 25 | $I_2$ | 2 | 4 | 100 | 40.2 | 46.2 | 9.4 |
| 16 | " | 25 | lauryl alcohol | 25 | " | 2 | 4 | 100 | 35.7 | 50.6 | 8.4 |
| 17 | " | 15 | n-octyl alcohol | 15 | " | 2 | 5 | 100 | 20.5 | 56.1 | 19.2 |
| 18 | " | 10 | " | 15 | " | 2 | 8 | 100 | 18.5 | 58.3 | 19.2 |
| 19 | Tetramethylphosphoramidic chloride | 25 | " | 15 | " | 2 | 5 | 100 | 19.7 | 55.3 | 21.4 |

Table I-continued

| Ex. No. | Ratio of amount of compounds used | | | | Reaction time (hr.) | Rate of conversion of tin (%) | Yields of $R_mSnX_{4-m}$ (%) | | |
|---|---|---|---|---|---|---|---|---|---|
| | Nitrogen-containing phosphorus compounds (g.) | Organic solvents (g.) | | $Br_2$, $I_2$ or compounds thereof (g.) | | | m=1 | m=2 | m=3 |
| 20 | Dimethylphosphoamidic dichloride 25 | methoxybutyl alcohol 15 | | " | 2 | 6 | 100 | 22.0 | 49.2 | 20.6 |
| 21 | " 25 | n-octyl alcohol 15 | | " | 2 | 6 | 100 | 21.2 | 52.0 | 21.4 |

EXAMPLE 22

30 g. of tin foil, 95 g. of n-octylchloride, 10 g. of triphenylphosphate, 40 g. of N-methyl pyrrolidone, 20 g. of n-octyl alcohol and 2 g. of iodine are placed in a 500 ml. flask with four necks equipped with a stirrer, a reflux condenser and a thermometer, heated under reflux at 185° to 190°C. for 6 hours, then 100% of the tin foil is reacted to give a yellow clear reaction mixture. The mixture is treated by a known chemical purification procedure to give octyltintrichloride, dioctyltindichloride and trioctyltinchloride in the yields of 43.9%, 42.1% and 10.1% respectively. The total yield of those three octyltinchlorides amounts to 95.2% based on the metallic tin employed.

EXAMPLES 23–37

The results of Examples 23–37 which are carried out according to Examples mentioned above are summarized in Table II in which 94.2 g. of n-octyl chloride is used, and the metallic tin employed is tin foil in all cases in an amount of 30 g. Compounds of the general formula

in which m is equal to 4 cannot be obtained in any one of the Examples.

Table II

| Ex. No. | Ratio of amount of compounds | | | | | | | Reaction time (hr.) | Rate of conversion of tin (%) | Yields of $R_mSnX_{4-m}$ (%) | | |
|---|---|---|---|---|---|---|---|---|---|---|---|---|
| | Organic solvents | (g.) | Phosphorus compounds | (g.) | Amine compounds | (g.) | $Br_2$, $I_2$ or compounds thereof | (g.) | | | m=1 | m=2 | m=3 |
| 23 | n-octyl alcohol | 10 | triphenyl phosphite | 10 | N-methyl pyrrolidone | 40 | $I_2$ | 2 | 4 | 100 | 18.0 | 68.8 | 9.6 |
| 24 | lauryl alcohol | 5 | diphenyl phosphorchloridate | 10 | " | 40 | " | 2 | 4 | 100 | 13.4 | 71.5 | 9.9 |
| 25 | n-octyl alcohol | 5 | triethyl phosphite | 10 | " | 40 | $AlBr_3$ | 4 | 4 | 100 | 10.5 | 73.7 | 10.1 |
| 26 | 2-ethylhexyl alcohol | 5 | " | 10 | " | 40 | $CuI_2$ | 4 | 4 | 100 | 12.0 | 78.5 | 5.0 |
| 27 | n-butyl alcohol | 40 | " | 5 | " | 40 | $I_2$ | 2 | 4 | 100 | 45.0 | 45.5 | 5.3 |
| 28 | 2-ethylhexyl alcohol | 10 | triphenyl phosphite | 20 | quinoline | 20 | $PBr_3$ | 5 | 3 | 100 | 10.9 | 45.0 | 34.8 |
| 29 | " | 10 | " | 20 | morpholine | 20 | $MgI_2$ | 5 | 4 | 100 | 12.3 | 39.9 | 36.9 |
| 30 | decyl alcohol | 10 | " | 20 | tributylamine | 20 | $MgBr_2$ | 5 | 3 | 100 | 11.8 | 39.2 | 40.4 |
| 31 | methoxybutyl alcohol | 10 | " | 20 | triphenylamine | 20 | $Br_2$ | 5 | 3 | 100 | 13.2 | 38.0 | 39.0 |
| 32 | 2-ethylhexyl alcohol | 10 | diphenyl phosphorchloridate | 10 | pyridine | 20 | $ZnBr_2$ | 5 | 3 | 100 | 11.6 | 40.2 | 38.3 |
| 33 | lauryl alcohol | 10 | tetraethyl phosphonium iodide | 20 | N,N-dimethylformamide | 20 | $ZnI_2$ | 4 | 4 | 100 | 12.7 | 35.6 | 40.6 |
| 34 | methoxybutyl alcohol | 5 | triphenyl phosphite | 20 | tributylamine | 20 | $I_2$ | 2 | 4 | 100 | 12.0 | 41.0 | 37.0 |
| 35 | 2-ethylhexyl alcohol | 25 | triphenyl phosphate | 20 | " | 20 | " | 2 | 3 | 100 | 36.2 | 40.0 | 15.3 |
| 36 | n-octyl alcohol | 5 | " | 20 | " | 20 | " | 2 | 5 | 100 | 12.6 | 41.0 | 36.5 |
| 37 | methoxybutyl alcohol | 25 | " | 20 | " | 20 | " | 2 | 3 | 100 | 34.9 | 48.1 | 6.2 |

What is claimed is:

1. A process for producing an octyltin chloride of the formula

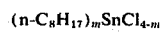

wherein m is an integer of 1 to 3, which comprises reacting n-octyl chloride with metallic tin in the presence of, as a first component, (1) a mixture of (a) a phosphorus compound selected from the group consisting of triethyl phosphite, tributyl phosphite, triphenyl phosphite, triphenyl phosphate, diphenyl phosphorchloridate and tetraethylphosphonium iodide, with (b) an amine compound selected from the group consisting of N-methyl pyrrolidone, quinoline, morpholine, pyridine, dibutylamine, tributylamine, triphenylamine and N,N-dimethylformamide, or (2) a nitrogen-containing phosphorus compound selected from the group consisting of hexamethylphosphoramide, dimethylphosphoramidic dichloride and tetramethylphosphoramidic chloride, together with, as a second component, at least one member selected from the group consisting of bromine, iodine, $PBr_3$, $AlBr_3$, $CuI_2$, $MgI_2$, $MgBr_2$, $ZnBr_2$ and $ZnI_2$ which are capable of evolving bromine or iodine at the reaction temperature employed, and as a third component, an organic solvent selected from the group consisting of n-butyl alcohol, methoxybutyl alcohol, 2-ethylhexyl alcohol, n-octyl alcohol, decyl alcohol and lauryl alcohol.

2. The process according to claim 1, wherein the reaction is carried out at a temperature of from 130°C. to 230°C. for from 3 to 20 hours.

3. The process according to claim 1, wherein the n-octyl chloride is used in an amount of 1.5 to 5 moles per mol of metallic tin.

4. The process according to claim 1, wherein the mixture of the phosphorus compound with the amine compound is used in an amount of at least 0.1% by weight based on the amount of metallic tin.

5. The process according to claim 1, wherein the nitrogen-containing phosphorus compound is used in an amount of at least 0.1% by weight based on the amount of metallic tin.

6. The process according to claim 1, wherein the second component is used in an amount of at least 0.01% by weight based on the amount of metallic tin.

* * * * *